US009459207B2

(12) United States Patent
Hanlon et al.

(10) Patent No.: US 9,459,207 B2
(45) Date of Patent: Oct. 4, 2016

(54) METHOD OF CHARACTERIZING INTERACTIONS AND SCREENING FOR EFFECTORS

(71) Applicant: Wyatt Technology Corporation, Santa Barbara, CA (US)

(72) Inventors: Amy D. Hanlon, Santa Barbara, CA (US); Michael I. Larkin, Santa Barbara, CA (US)

(73) Assignee: WYATT TECHNOLOGY CORPORATION, Goleta, CA (US)

( * ) Notice: Subject to any disclaimer, the term of this patent is extended or adjusted under 35 U.S.C. 154(b) by 0 days.

(21) Appl. No.: 14/838,258

(22) Filed: Aug. 27, 2015

(65) Prior Publication Data
US 2015/0369732 A1    Dec. 24, 2015

Related U.S. Application Data

(62) Division of application No. 13/578,593, filed as application No. PCT/US2011/026287 on Feb. 25, 2011.

(60) Provisional application No. 61/310,133, filed on Mar. 3, 2010.

(51) Int. Cl.
*G01N 21/00* (2006.01)
*G01N 21/49* (2006.01)
(Continued)

(52) U.S. Cl.
CPC ........... *G01N 21/49* (2013.01); *G01N 15/0211* (2013.01); *G01N 15/1429* (2013.01);
(Continued)

(58) Field of Classification Search
CPC ............... G01N 2015/0222; G01N 15/0211; G01N 2015/0038; G01N 2015/0092; G01N 2015/0216; G01N 21/4738; G01N 21/49; G01N 21/51

See application file for complete search history.

(56) References Cited

U.S. PATENT DOCUMENTS 6,788,409 B2 * 9/2004 Goodwin ............... G01N 15/04
356/339
2011/0293605 A1 * 12/2011 Sathish ............. C07K 16/2818
424/133.1

OTHER PUBLICATIONS

Hanlon, A.D., M.I. Larkin, R. M. Reddick, Free-Solution, Label-Free Protein-Protein Interactions Characterized by Dynamic Light Scattering, Biophysical Journal, Jan. 2010, pp. 297-304, V. 98, Biophysical Society, USA.

(Continued)

*Primary Examiner* — Kara E Geisel
*Assistant Examiner* — Rufus Phillips
(74) *Attorney, Agent, or Firm* — David N. Villalpando; Philip J. Wyatt

(57) ABSTRACT

This invention enables high throughput detection of small molecule effectors of particle association, as well as quantification of association constants, stoichiometry, and conformation. "Particle" refers to any discrete particle, such as a protein, nucleic acid, carbohydrate, liposome, virus, synthesized polymer, nanoparticle, colloid, latex sphere, etc. Given a set of particle solutions having different concentrations, dynamic light scattering measurements are used to determine the average hydrodynamic radius, $r_{avg}$, as a function of concentration. The series of $r_{avg}$ as a function of concentration are fitted with stoichiometric association models containing the parameters of molar mass, modeled concentrations, and modeled hydrodynamic radii of the associated complexes. In addition to the $r_{avg}$ value analysis, the experimental data may be fit/analyzed in alternate ways. This method may be applied to a single species that is self-associating or to multiple species that are hetero-associating. This method may also be used to characterize and quantify the association between a modulator and the associating species.

7 Claims, 6 Drawing Sheets

(51) Int. Cl.
   *G01N 21/47*   (2006.01)
   *G01N 15/14*   (2006.01)
   *G01N 15/02*   (2006.01)
   *G01N 15/00*   (2006.01)

(52) U.S. Cl.
   CPC ...... *G01N15/1434* (2013.01); *G01N 21/4738* (2013.01); *G01N 2015/0038* (2013.01); *G01N 2015/0092* (2013.01); *G01N 2015/0216* (2013.01); *G01N 2015/0222* (2013.01); *G01N 2201/06113* (2013.01); *G01N 2201/12* (2013.01)

(56) References Cited

OTHER PUBLICATIONS

Sharma, P., D. Rajalingam, T.K.S. Kumar, S. Singh, A Light Scattering Study of the Interaction of Fibroblast Growth Factor (FGF) with its Receptor, Biophysical Journal: Biophysical Letters, 2008, pp. L71-L73, Biophysical Society, USA.

\* cited by examiner

US 9,459,207 B2

METHOD OF CHARACTERIZING INTERACTIONS AND SCREENING FOR EFFECTORS

PRIORITY

This application claims priority to U.S. non-provisional Application Ser. No. 13/578,593 filed Mar. 11, 2013, which is the National Stage Entry of International Application PCT/US11/26287 with an International Filing Date of Feb. 25, 2011 which in turn claims priority to U.S. provisional application Ser. No. 61/310,133 filed Mar. 3, 2010, "Method of high throughput detection of small molecule effectors of particle interactions, as well as derivation of particle binding stoichiometry and equilibrium association constants."

BACKGROUND

The high throughput detection of small molecule inhibitors and/or enhancers of particle interaction is desired in many fields of science. By "particle," we refer to such objects as protein and polymer molecules together with their conjugates and co-polymers, viruses, bacteria, virus-like particles, liposomes, polystyrene latex emulsions, nanoparticles, and all such particles within the approximate size range of one to a few thousand nanometers. Dynamic light scattering provides an excellent analysis method for screening large chemical libraries, such as small molecule libraries of compounds, for effectors of particle interactions. Such libraries are typically available at molecular screening centers, such as the Scripps Research Institute Molecular Screening Center in Jupiter, Fla., the Broad Institute in Cambridge, Mass., the Molecular Screening Shared Resource centered at the University of California, Los Angeles, and others. Small molecule libraries of compounds may also be held by companies, private individuals, foundations, etc. Compound collections can exceed 300,000 molecules that possess diverse architecture and function. Depending on the particles used, the high throughput screening of chemical libraries can lead to a greater understanding of cellular function, the discovery of new drugs, or any variety of nanotechnology-related innovations.

Additionally, libraries of macromolecules, such as a library of a proteins subjected to site directed mutagenesis at a large number of sites, may also be screened to identify which residue(s) modulate/change interactions with the binding partner(s). Additionally libraries of nanoparticles, such as gold particles or quantum dots, may also be screened against binding partners using this method. Alternatively, a nucleic acid fragment library could be screened against a protein to determine which region the protein may bind to. The aforementioned screen types could be done in the presence or absence of small molecule modulators. Any particle type can potentially be screened in this manner.

The detection and characterization of reversible associations of particles in solution is also essential in many areas of science. For illustrative purposes, we shall focus specifically upon the interactions of protein molecules and their conjugates, though the techniques disclosed will be equally applicable to all the other particle types listed. Whenever the word "molecule" is used within this specification, it will be understood that the word "particle" may be substituted therefore in most cases without any limitations implied upon the inventive methods described. The study and measurement of molecular associations is important for many reasons; whether to gain understanding of cellular function or to develop and formulate pharmaceuticals or other biologically active materials. Essentially, most pharmaceuticals have functionality due solely to association with molecules within the body, so the discovery and accurate characterization of these associations is a key element for pharmaceutical development.

Molecules of the same species may self-associate to form dimers, trimers, and higher order complexes, whereas molecules of different species may associate with each other to yield complexes of various compositions. More than two particle types may combine to form a complex. Such associations may be reversible or irreversible. For reversible associations, the binding affinities are characterized by a unique equilibrium constant. The equilibrium constant specifies the relative concentrations of the complex(es) and the component monomers for a given set of conditions. According to Le Châtlier's principle, every closed system must eventually reach equilibrium. When reactants in a reversible process are in excess of their equilibrium concentrations, the reaction proceeds to convert the reactants to products and achieve equilibrium. Alternately, when products are in excess, the reaction proceeds in a reverse direction to convert product to reactant and again achieve equilibrium. For the reaction of molecules A and B to form the complex AB, $A+B \rightleftharpoons AB$, the equilibrium association constant is written:

$$K_a = \frac{[AB]}{[A][B]},$$

where the bracketed terms correspond to the corresponding concentrations of the molecules A, B, and their complex AB. Although constant under stable conditions, the equilibrium constant of a given association may change in response to environmental factors, such as temperature, buffer salinity, or the presence of other factors modulating the interaction.

There are many techniques used to measure equilibrium constants and characterize molecular associations. However, the majority can detect only tightly bound interactions, and require the tagging/labeling or immobilization of one of the binding partners. As any modification of the molecule can potentially influence the interaction, techniques implementing free-solution testing are optimal. "Free-solution" means that molecules are neither tagged/labeled nor immobilized for analysis. As no molecule-specific immobilization/tagging protocol is required, free solution techniques are not limited to a single molecular type, such as proteins. Free solution techniques are applicable to most molecular types.

There are several well-established free-solution methods to determine stoichiometry and equilibrium constants, such as calorimetry and sedimentation equilibrium. Static light scattering is another option. The theory of using static light scattering measurements at different solution concentrations to determine self or hetero association constants has long been known, cf. Huglin, 1972 *Light Scattering From Polymer Solutions*, Academic Press, London and New York, by W. Burchard and J. M. G. Cowie in Section 17, Selected Topics in Biopolymeric Systems, as well as Hirs, 1973, *Methods in Enzymology Volume XXVII, Enzyme Structure, Part D*, Academic Press, London and New York, by Pittz et al. in section 10, Light Scattering and Differential Refractometry. Such measurements were demonstrated fairly recently by T. Yamaguchi et al. in *Biochem. Biophys. Res. Commun.*, 2002, Vol. 290, 1382-1387 and improved upon by Attri et al., in *Anal. Biochem.,* 2005, Vol. 346, 132-138, where they termed the technique "concentration gradient light scattering".

In static light scattering, the intensity of scattered light is proportional to the molar mass of the molecule; a dimer scatters twice as much light as two monomers. For example, in the study of self-association, the static light scattering concentration gradient method measures the intensity of scattered light over a series of concentrations of the molecule studied. The scattered light changes for each concentration, in accordance with the change in the population of the associated species. The association constant quantifies how the associated species change at different concentration ratios. To determine the association constant and stoichiometry of the interaction, the experimental data are fit against models that estimate the concentrations of the individual components present at each solution concentration.

The three free-solution methods, static light scattering, calorimetry, and sedimentation equilibrium, require a relatively large amount of sample when used in their standard configurations. Techniques requiring minimal sample quantities for measurement are often required, as the required molecules may not be available in sufficient quantities, as synthesis or isolation and purification can present significant challenge and expense. Finally, none of the three methods are suitable for high-throughput measurement. Thus, the low productivity characteristics of all three methods impede practical study spanning a large compositional range.

Recently, a fourth free-solution method has been explored: back-scattering interferometry with high-throughput capability and very low sample requirements. Cf Bornhop et al. *Science* 317, pages 1732-1736 (2007). Unfortunately, this method is limited to systems that bind in a 1:1 ratio. Other stoichiometries, which commonly occur in nature, cannot be distinguished or characterized.

The search for a free-solution, high-throughput method with low sample requirements and the ability to detect multiple binding stoichiometries remains. To date, no such method has been reported. Our inventive method, on the other hand, based on the use of dynamic light scattering resolves, thereby, the previously discussed problems.

Dynamic light scattering is a well-established technique, typically used to determine the diffusion coefficients of scattering particles in solution and, from them, an associated set of hydrodynamic radii. The hydrodynamic radius is the radius of a hard sphere whose diffusion coefficient is the same as that measured for the sample particle. Dynamic light scattering, also known as quasi-elastic light scattering, or QELS, uses the measured fluctuations in the light scattered from a sample to determine these quantities. When in solution, sample particles are buffeted by the solvent molecules. This leads to a random motion of the particles called Brownian motion. As light scatters from the moving particles, this random motion imparts a randomness to the phase of the scattered light, such that when the scattered light from two or more particles is combined, a changing intensity of such scattered light due to interference effects will occur. The dynamic light scattering measurement of the time-dependent fluctuations in the scattered light is achieved by a fast photon counter. The fluctuations are directly related to the rate of diffusion of the particles through the solvent. The fluctuations are then analyzed to yield diffusion coefficients and, from these, the hydrodynamic radii of the sample.

The time variations of the intensity fluctuations are quantified by means of so-called autocorrelation techniques. Depending upon the experimental configuration of the dynamic light scattering instrumentation, the resulting autocorrelation function may be an intensity-intensity or field-field autocorrelation function, or a combination of these two. The intensity-intensity correlation function is $$g^{(2)}(\tau) = \frac{\langle I(t)I(t+\tau)\rangle}{\langle I(t)\rangle^2} \quad (1)$$

where I(t) is the intensity of the scattered light at time t, and the brackets indicate averaging over all t. The correlation function depends on the delay $\tau$, that is, how the intensity variation in time t+$\tau$ correlates to the intensity variation in t. FIG. 1 shows a typical correlation function for a sample of Immunoglobulin G protein in solution. In this figure open triangles are data, and the solid line is a fit of the data to a simple exponential function, described below.

As described in various light scattering texts, cf. B. Chu, *Laser Light Scattering: Basic Principles and Practice*, (Academic Press, Boston, 1991), for a single particle freely diffusing in solution, the correlation function of Eq. 1 becomes $$g^{(2)}(\tau)=B+\beta \exp(-2\Gamma\tau) \quad (2)$$

where B is the baseline of the correlation function at infinite delay ($\tau\to\infty$), $\beta$ is the correlation function amplitude at zero delay ($\tau=0$), and $\Gamma$ is the decay rate.

An algorithm is used to fit the measured correlation function to Eq. (2) to retrieve $\Gamma$. From this point, the diffusion coefficient for the particle, D, is calculated from $\Gamma$ from the relation, $$D = \frac{\Gamma}{q^2}.$$

Here, q is the magnitude of the scattering vector, i.e.

$$q = \frac{4\pi n_0}{\lambda_0}\sin(\theta/2),$$

where $n_0$ is the solvent index of refraction, $\lambda_0$ is the vacuum wavelength of the incident light, and $\theta$ is the scattering angle. Finally, the hydrodynamic radius $r_h$ of an equivalent diffusing sphere is derived from the Stokes-Einstein equation, $$r_h = \frac{k_B T}{6\pi\eta D},$$

where $k_B$ is the Boltzmann constant, T is the absolute temperature, and $\eta$ is the solvent viscosity.

Since it is relatively insensitive to stray background light from the walls of the containing structures, dynamic light scattering measurements may be made from very small sample volumes, thus reducing sample quantity requirements and enabling the use of high throughput measurements. As such, dynamic light scattering may be used with microtiter plate based systems or very small volume cuvettes, each such sample holding element containing only a few microliters of sample. Although such measurements require a higher concentration of sample relative to those needed for static light scattering measurements, the smaller sample volumes typically result in a significant overall reduction in total sample quantity required.

The application of the static light scattering concentration gradient procedures to dynamic light scattering, DLS, would be a significant improvement for determining particle association stoichiometry and affinity, as this would permit far smaller sample quantities, as well as high throughput processing. For the static light scattering method, as each different sample composition is examined, an associated excess Rayleigh ratio is measured. Such Rayleigh ratios are related directly to the molecular species producing them. A dynamic light scattering measurement, on the other hand, yields a correlation function derived from the scattered light fluctuations attributed to these same molecular species. Such correlation functions may be decomposed, following certain assumptions, to represent the distributions, in terms of diffusion coefficients and their associated hydrodynamic radii, of the scattering molecules.

Whereas static light scattering data are relatively easy to model in terms of postulated associated states, DLS responses to the presence of such states are far more complex. For example, the molar mass of a molecular homodimer scatters four times the amount of light as one of its two monomers, or twice as much light as scattered by the two separated monomers. On the other hand, the difference of the diffusion coefficient of a dimer from that of one of its composite monomers depends critically upon the structure of the associated dimer. Considering just the corresponding hydrodynamic radii as a measure of these differences, there may be a range of values, whereas for the static light scattering case there is a known discrete value.

The application of dynamic light scattering, for obtaining molecular association constants and stoichiometries by modeling thereof a series of relative concentration gradients has been attempted infrequently over the past four decades, although DLS techniques are frequently used to study irreversible particle association, particularly particle aggregation. Examples of such prior work are described by Claes, et al. in Chapter 5, An on-line dynamic light scattering instrument for macromolecular characterization, of *Laser Light Scattering in Biochemistry* Eds. S. E. Harding, et. al., 1992, The Royal Society of Chemistry, Cambridge, UK, and Wilson *Journal of Structural Biology* 142, 56-65 (2003).

Self association was studied by Mullen et al., *J. Mol. Biol.* 1996, 262, 746-755, MacColl et al., *Biochemistry* 1998, 37, 417-423, an Lunelli, *Physical Review Letters* 1993, 70(4), 513-516. In the dynamic light scattering industry, Protein Solutions developed a "Fraction Calculator" in an early version of the Dynamics software to determine the fraction of each species in a binary equilibrium, using the average $r_h$ and postulating or measuring the two end points. Malvern also has recently published an application note that proposes how the percent monomer in a monomer/dimer system can be estimated using the hydrodymic radius of the mixture.

In terms of heteroassociations, Vannini et al., *J. Biol. Chem.*, 2004, Vol. 279, Issue 23, 24291-24296, used dynamic light scattering to predict the stoichiometry of a protein complex by isolating the complex and estimating the molecular mass of the complex from the hydrodynamic radius. This study involved a complex that could be isolated from the component protein monomers, indicating the association was irreversible or very tightly bound. DLS measurements have also been performed at a series of two or more ratios of two components such as the work by Wang et al., *Biopolymers*, 1981, v.20, p 155-168, Murphy et al., *Biophysical Journal*, 1988, 54, 45-56, Leliveld S. R. et al., *Nucleic Acids Research*, 2003, Vol. 31, No. 16, 4805-4813, and Sharma et al., *Biophysical Journal: Biophysical Letters*, 2008, L71-L73.

BRIEF DESCRIPTIONS OF THE DRAWINGS

FIG. 1 shows an autocorrelation function derived from a solution of Immunoglobulin G protein.

FIG. 2 compares two models used to estimate the hydrodynamic radius of associating species.

BRIEF DESCRIPTION OF INVENTION

Figure 1:
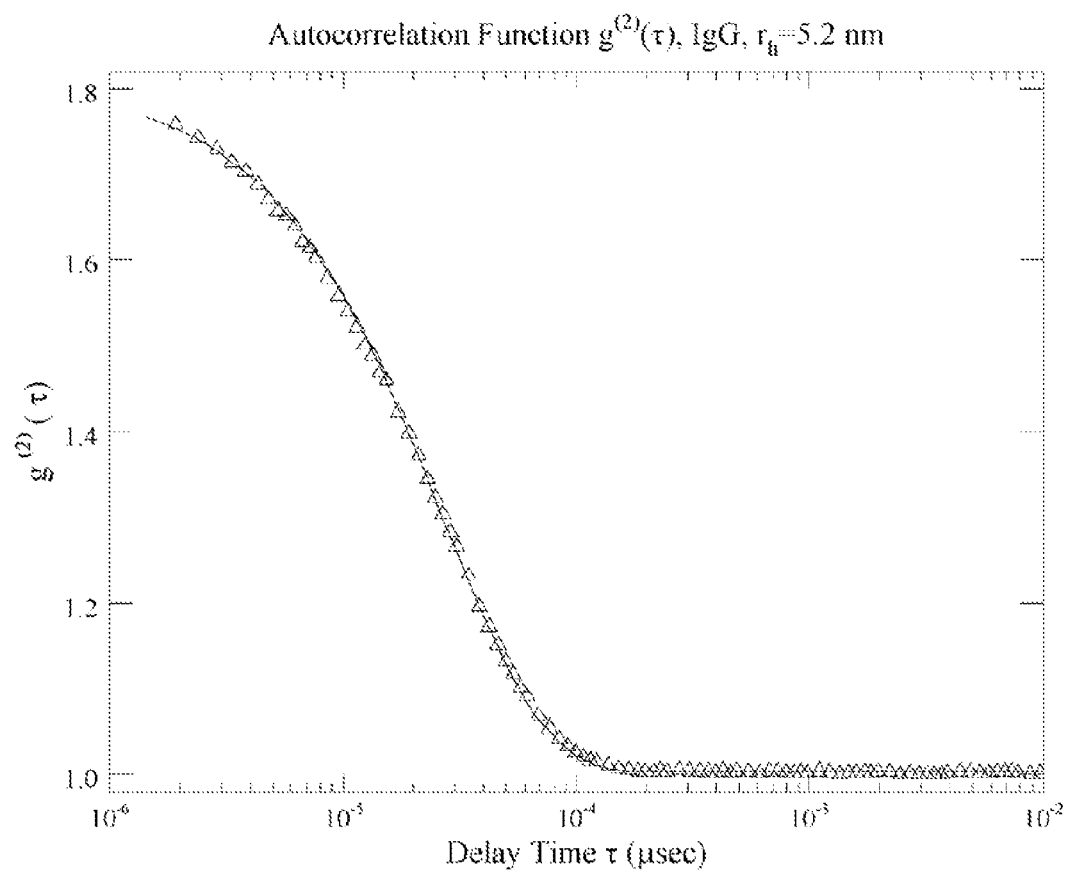

As previously discussed, methods of observing particle association with DLS has been explored for some time, however, the further step of measuring a comprehensive series of concentrations or ratios, followed by parametric modeling and calculation of association constants, stoichiometry, and conformations had neither been proposed nor demonstrated prior to the inventive methods described in the publication, authored in part by the inventors, Hanlon et al. "Free-solution, label-free protein protein interactions characterized by dynamic light scattering" Biophysical Journal, 2010, v.98, p 297-304, and described herein. We also specify that the method described in the paper may be used to identify the optimal ratio of two proteins for achieving the maximum amount of association, and thus the largest average solution hydrodynamic radius. This ratio can then be used to screen for small molecule chemical inhibitors, as inhibition would then result in the largest possible change in solution hydrodynamic radius. Although the optimized ratio may often be the best choice for a large scale screen, other ratios may be used. This technique is also not limited solely to screening of inhibitors, as other effectors/modulators may also be identified with the inventive method described herein.

An additional benefit of this method is that it may be used to pre-screen the chemical libraries for aggregation. Aggregated compounds can act as "promiscuous" inhibitors, and yield false positive. Dynamic light scattering is an excellent way of testing for these aggregates, as documented in Feng et al., *Nature Chemical Biology*, 2005, v.1, p. 146-148.

High throughput screening for effectors which modulate the solution viscosity by effecting changes on the interacting particles may also be identified by this method, although an internal standard such a nano-sized polystyrene sphere or other internal standard may be employed in the sample solution. DLS measurement of solution viscosity was recently detailed by He et al., "High throughput dynamic light scattering for measuring viscosity of concentrated protein solutions," *Analytical Biochemistry*, 2010, accepted for publication.

The key objective of the present invention is to provide a high throughput method for identification of small molecule effectors/modulators of particle interactions through the screening of large chemical libraries, using dynamic light scattering to monitor changes in hydrodynamic radius of optimized or non-optimized solutions. An additional objective is to provide a high throughput method of screening for said effectors using another aspect of DLS data, such as a change in the measured viscosity, time dependent changes, or some other variable determined by DLS.

An additional objective is to provide a high throughput method of screening libraries of particles.

An additional objective of the inventive method disclosed is the means by which all of the stoichiometry and association constants that are extracted from the static light scattering concentration gradient method, are derived equivalently from DLS measurements, with the additional yield of associated species conformational information.

An additional objective of our inventive method is to provide means to reduce the total quantity of sample required for extraction of said stoichiometry and association constants.

A further objective of our inventive method is the establishment of a suitable means by which the hydrodynamic radius of each complex may be modeled using the hydrodynamic radii of its constituent molecules.

A further objective of our invention is to permit all measurements to be made at considerably greater speed by means of a high throughput device.

Another objective of our inventive method is the ability to measure the association constants under a variety of different environmental conditions such as temperature, storage periods, packaging, etc.

A further objective of our invention is to characterize the effects, of small molecules that may modulate protein associations. Our invention allows the characterization of the association constants between the associating particles and their modulators.

An inventive free-solution method is described that uses dynamic light scattering for the high throughput detection of small molecule effectors of particle interactions. The method may also be used to screen libraries of particles. The method may also be used to characterize the equilibrium association constants and the stoichiometry of reversible complexes. The method is high-throughput with low sample requirements For self-association, a series of solutions are made containing different concentrations of the sample molecule, all in the same solvent. For heteroassociation, the method begins with the mixing of two stock solutions, one of each molecule in the same solvent, at varying ratios beginning, for example, with 100% of the first molecule and 0% of the second molecule and ending with 0% of the first molecule and 100% of the second molecule. Any other series of varying ratios may be used, as well. Additionally, for either self- or hetero-association determinations, a modulator may be added to the solutions, and its effects quantified.

Each member solution of the series so prepared is generally illuminated with a fine laser beam and the fluctuating light scattered by said member is processed to yield its corresponding autocorrelation function. The resultant autocorrelation function data, one data set for each member ratio prepared, are then processed according to the following four-step procedure: 1) Modeling the relative concentration of each molecular component in solution: The concentrations of all components in a solution at a given time are calculated from postulated stoichiometries, association constant(s), $K_a$, and the known a priori concentrations of the stock solutions of the constituent molecule(s). 2) Modeling the translational diffusion coefficient for associated molecules: Models describing the conformation of associating species are parameterized and then used to calculate the translational diffusion coefficient, and thence its hydrodynamic radius, $r_h$, for each of the self- or hetero-associated species. 3) Modeling DLS data based upon above concentration and associated $r_h$ models: DLS results are calculated based on the known molar masses, the parameterized relative species concentrations, and the parameterized translational diffusion coefficients. 4) Fitting modeled DLS results to DLS measurements: The parameterized DLS results are then compared to the actual DLS measurements and a best fit of the parameters derived. A variety of different parameterized models of association constants may then be compared to a single datum or set of data. In this manner, the most probable parameter values are derived. Alternatively, of course, a specific parameter set may be assumed ab initio, and the corresponding stoichiometry and association constant or constants of the complexes in solution determined.

Following the initial characterization, the particle mixture demonstrating the highest hydrodynamic radius may be used for a large scale screen of chemical libraries, where a drop in the solution hydrodynamic radius is a positive hit of the screen.

Alternately, the solution may be optimized to demonstrate an increase of the solution hydrodynamic radius to screen for an association promoter, or any change in signal as determined by the user to be the most indicative of the desired effect.

In addition, libraries of modified/altered particles may be screened against the reacting partner(s). The most substantial change in the solution hydrodynamic radius could be interpreted as the most promising hit.

In addition, multiple systems could be screened simultaneously.

DETAILED DESCRIPTION OF THE INVENTION

For illustrative purposes, we shall focus specifically upon the interactions of protein molecules, though the techniques disclosed are applicable to all the other particle types as specified in the Background section of this specification. Again, whenever the term "molecule" is used, it will be understood that the word "particle" may be substituted therefore in most cases without any limitations implied upon the inventive method.

The method begins with sample preparation to be described presently. The DLS data are collected, and then analyzed in a four-step procedure. First, the concentrations of all components in a solution at a given time are calculated from postulated stoichiometries, association constant(s), $K_a$, and the known a priori concentrations of the stock solutions of the constituent molecule(s). Second, the translational diffusion constant, and hence its corresponding hydrodynamic radius, of each associated species is modeled. Third, the modeled concentration data and modeled hydrodynamic radius data are combined to model the expected dynamic light scattering data at each sample ratio. Fourth, a best fit of the models to the collected DLS data is obtained. Thus, some or all parameters are adjusted to produce a best fit to the DLS data. Such fitting might be achieved using a least squares method, for example. These four steps of data analysis are discussed in detail in the following, and variations are possible, as would be apparent to one skilled in the art of DLS or particle associations.

There are many different ways of preparing samples in varying concentrations or ratios, and there are many different DLS systems capable of making the measurements required for our invention. A series of different concentrations, or ratios of two components, may be made manually, or automatically. Automatic methods include commercially available fluid handling robots, inline dilution/concentration systems, automated multiple syringe systems, autosamplers with pre-treatment capability, etc. Below we outline one such sample preparation and one such measurement system based on the use of a high throughput method using microtiter plates.

In this example, to prepare the sample series for both self- and hetero-association, two stock solutions are mixed manually. For analysis of hetero-association, a high concentration, on the order of 0.5 mg/mL, solution of each pure molecule is prepared in the same solvent. For larger molecules, such as those greater than, say, 50 kDa, lower concentrations may be used. For analysis of self-association reactions, the molecular solution is prepared at the highest concentration to be tested; the second solution is the pure solvent in which the sample molecule was prepared. All solutions are filtered through a 0.02 μm filter.

For either type of analysis, aliquots of the two solution mixtures are dispensed into a 1536 well microtiter plate in a series of ratios from 100% A:0% B to 0% A:100% B, or some subset thereof, where the number of ratios prepared depends upon the desired detail of analysis. Typically, 10-20 ratios are used.

Following the dispensing of the sample, the microtiter plate is centrifuged at a rate and duration sufficient to remove any bubbles present in the samples; typically 1000 g for 15 seconds. Wells may then be covered to avoid evaporation, for example, by dispensing approximately 10 μL of paraffin oil into each well. The plate is then re-centrifuged prior to being placed into a dynamic light scattering instrument programmed, for example, to make 25 one-second dynamic light scattering measurements per well.

Other sample holding systems may be used for with this inventive method. Multiwell plates are only one possibility.

Step 1: Modeling Concentrations of all Components in Solution

For the reaction $A+B \rightleftharpoons AB$ the equilibrium association constant is given as $$K_{AB} = \frac{[AB]}{[A][B]}.$$

For known total molar concentrations of two species $[A_{tot}]$ and $[B_{tot}]$, and known or modeled association constant, the molar concentrations of free solution unassociated [A] and [B] and molar concentrations of associated species, such as [AB], may be derived by fitting the data to the model selected. DLS measurements are made of each mixture over a range of $[A_{tot}]:[B_{tot}]$ ratios to provide sufficient data to extract the reaction equilibrium constant in terms of the model selected. This basic approach may be applied generally to species that are reversibly self- and/or hetero-associating with any assumed stoichiometry, as shown, for example by Cantor and Schimmel, Chapter 15, "Ligand interactions at equilibrium" in *Biophysical Chemistry, Part III: The Behavior of biological macromolecules*, W.H. Freeman and Company, New York, N. Y., 1980. Three examples are given below.

EXAMPLE 1

Hetero-Association: $A+B \rightleftharpoons AB$

Species A and B associating to form species AB with equilibrium association constant $K_{AB}$:

$[A_{tot}]=[A]+[AB]$

Equation $[B_{tot}]=[B]+[AB]$ $[AB]=K_{AB}[A][B]$ which reduces to:

$$[A] = \frac{[A_{tot}]}{(1+K_{AB}[B])}$$

$$[B] = \frac{1}{2}\left\{([B_{tot}]-[A_{tot}]) - \frac{1}{K_{AB}}\left(1-\{1+2K_{AB}([B_{tot}]+[A_{tot}])+K_{AB}^2([B_{tot}]-[A_{tot}])^2\}^{\frac{1}{2}}\right)\right\}$$

EXAMPLE 2

Self-Association: $A+A \rightleftharpoons AA$

Species A self-associating to form species AA with equilibrium association constant $K_{AA}$:

$[A_{tot}]=[A]+2[AA]$ $[AA]=K_{AA}[A]^2$

Which reduces to:

$$[A] = \frac{1}{4K_{AA}}\left(\{1+8K_{AA}[A_{tot}]\}^{\frac{1}{2}} - 1\right)$$

EXAMPLE 3

Three Binding Components: $A+B \rightleftharpoons AB$, $A+C \rightleftharpoons AC$ Species A, B, and C, associating to form species AB and AC with association constants $K_{AB}$ and $K_{AC}$. This example pertains to association modulators. Consider species A and B to be the primary associating species, and species C to be a modulator of those associations, e.g. a small molecule inhibitor. In this case, the presence of [AC] reduces the availability of free [A] in solution, and so reduces the quantity of [AB] in solution. The molar concentrations of all species may be found using the set of equations:

$[A_{tot}]=[A]+[AB]+[AC]$ $[B_{tot}]=[B]+[AB]$ $[C_{tot}]=[C]+[AC]$ $[AB]=K_{AB}[A][B]$ $[AC]=K_{AC}[A][C]$ The above five equations may be reduced to a set of three equations and three unknowns, and solved.

To one skilled in the art it is clear that using the above technique we may model the concentrations in solution for any combination of A and B with any stoichiometry. It is also clear to one skilled in the art that any number of species inter-associating may be similarly modeled, and that self-association may be modeled simultaneously with heteroassociation.

Step 2: Modeling Translational Diffusion Coefficient for Associated Species

Figure 2:
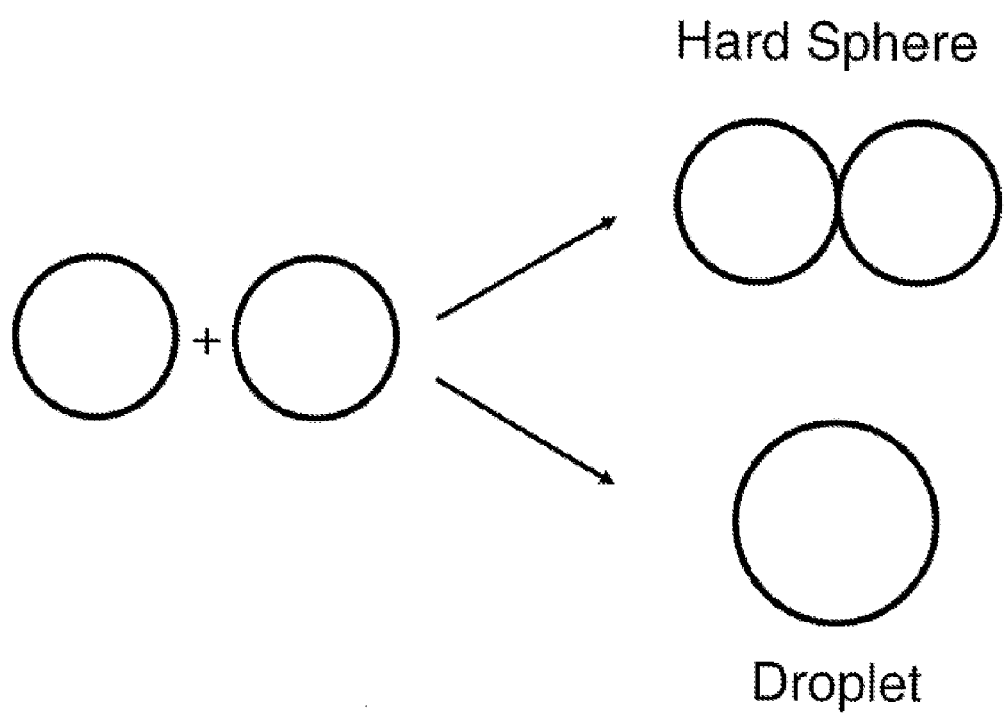

For species that are associating, the net size of the associating species will be larger than the size of the individual component species, and the corresponding translational diffusion coefficient will be smaller than that of the component species. In general, it is not possible to exactly calculate the size and shape of the associating species, although in special cases additional information may provide an estimate of the size, or constrain the possible sizes. There are many ways to model the hydrodynamic radius of associating species for example, those shown in FIG. 2 and several of which are discussed below:

1) Assume hard spheres. For combinations of hard spheres touching at single points, the translational diffusion coefficient and corresponding hydrodynamic radii may be calculated numerically as shown by J. G. de la Torre and V. A. Bloomfield in *Biopolymers*, Vol. 16, 1747 (1977). For example, for an association consisting of two hard spheres of equal radii r touching at a point, the translational diffusion coefficient of the associating object is found to be ¾ of the translational diffusion coefficient of one of the constituent objects. The hydrodynamic radius for that object is therefore 1.33 times the hydrodynamic radius for a single hard sphere. A model assuming hard sphere associations with a linear conformation will give the maximum reasonable hydrodynamic radius for a composite object, unless by associating with each other the basic shape of the constituent objects change.

2. Assume "droplet"—the mass changes to some power of the radius. The volume and radius of a sphere are related by the relation $v=4/3\pi r^3$. For two spheres of radii $r_1$ and $r_2$ which associate into one large sphere where the volumes are conserved, the resulting radius of the large sphere will be $r=\{r_1^3+r_2^3\}^{1/3}$. This "droplet" model of association, where the constituent species act as droplets of fluid combining to form a larger droplet, results in the most compact possible associating structure and the smallest possible change in hydrodynamic radius. Given this model, for two constituent objects having the same radius, the radius of the composite object will be $2^{1/3}=1.26$ times the radius of the constituent objects. While many systems may be well approximated by droplets coming together, others clearly will not. However, the increase in the hydrodynamic radius may be modeled in a similar way for objects that do not have the density of hard spheres. Proteins which are folded, for example, are found to generally have a hydrodynamic radius which varies as the molar mass to the power of 1/(2.34), rather than the power of ⅓ as would be expected for hard spheres as described by Claes, et al. in Chapter 5 of *Laser Light Scattering in Biochemistry* Eds. S. E. Harding, et. al., 1992, The Royal Society of Chemistry, Cambridge, UKHarding et al. Proteins are coiled and folded, rather than being solid, and so this result is not surprising. Proteins which are associating with one another will likely not form as compact a structure as a protein which simply folds, and so it is reasonable to assume that associating proteins could have a hydrodynamic radius which varies as the molar mass to the power (1/a), where a is a number less than 2.34. By this line of reasoning, we may model the hydrodynamic radius of an associating species as $$r = \left\{\sum_i r_i^a\right\}^{\frac{1}{a}}$$

where a may be fixed to some value, or may be allowed to vary as a parameter when fitting. From the above discussion it is clear that the way in which constituent objects associate has a significant bearing on the hydrodynamic radius of the composite object. For two objects of equal radii r associating, the hard sphere model yields 1.33r, the droplet model with a=3 yields a hydrodynamic radius for the composite object of 1.26r, and the droplet model with a=2 yields 1.41r. We demonstrate below that the inventive methods may be used to estimate the way in which species associate, and so provide valuable information regarding the conformation association.

Step 3: Modeling DLS Data Based Upon Above Concentration and Associated $r_h$ Models DLS measurements determine either the field-field or the intensity-intensity autocorrelation function, for a single or multiple species in solution, as described by Chu, in sections 3 and 4 of *Laser Light Scattering, Basic Principles and Practice* (2nd Ed., Dover Publications, Mineola New York (2007)). For a single species in solution, the functions are relatively simple. Polydisperse solutions, i.e., solutions containing non-identical species, have autocorrelation functions with greater complexity.

The field-field autocorrelation function, $g^{(1)}(\tau)$, of a single species undergoing thermal translational diffusion (Brownian motion) is a simple exponential function given as $$g^{(1)}(\tau)=\exp(-\Gamma\tau)$$

where $\tau$ is the autocorrelation delay time, $\Gamma$ is the decay rate given by $$\Gamma=q^2 D \qquad (3)$$

where D is the translational diffusion coefficient, and q is the scattered wave vector given by $q=(4\pi n/\lambda_0)\sin(\theta/2)$, where n is the solvent refractive index, $\lambda_0$ is the vacuum wavelength of the light used in the measurement, and $\theta$ is the scattering angle. For a spherical object of radius r, the translational diffusion coefficient is given by the Stokes-Einstein relation $$D = \frac{k_B T}{6\pi\eta r} \qquad (4)$$

where $k_B$ is the Boltzmann constant, T is the absolute temperature, and $\eta$ the solution viscosity. The above theory is detailed by F. Reif in section 15.6 of *Fundamentals of Statistical and Thermal Physics* (McGraw-Hill, New York (1965)). The hydrodynamic radius $r_h$ measured in a DLS experiment is the radius of a sphere having the same translational diffusion coefficient as the species under study, and as such is considered an equivalent spherical radius.

The intensity-intensity autocorrelation function, $g^{(2)}(\tau)$, for a single species in solution is related to the field-field autocorrelation function by the Seigert relation $$g^{(2)}(\tau)=1+\beta[g^{(1)}(\tau)]^2$$

where the amplitude $\beta$ is related to the number of coherence areas viewed in a measurement volume. For a single species in solution, the intensity-intensity autocorrelation function therefore becomes $$g^{(2)}(\tau)=1+\beta\exp(-2q^2 D\tau).$$

By measuring the normalized photon count autocorrelation function, the intensity-intensity autocorrelation function is obtained. For a single species solution, the data may be fit to a simple exponential function, as shown in FIG. 1, and the hydrodynamic radius may be extracted from the decay rate.

For polydisperse solutions, the analysis becomes more complex. In this case the field-field autocorrelation function is the sum over the decay rates of all the species in solution, weighted by the relative amount of light scattered into the detector by each species, such that $$g^{(1)}(\tau) = \int_0^\infty G(\Gamma)\exp(-\Gamma\tau)d\Gamma \quad (5)$$

Here, $G(\Gamma)d\Gamma$ is the fraction of scattered light intensity due to species with decay rates from $\Gamma$ to $\Gamma+d\Gamma$. The intensity-intensity autocorrelation function therefore becomes:

$$g^{(2)}\tau = 1 + \beta\left[\int_0^\infty e^{-\Gamma\tau}G(\Gamma)d\Gamma\right]^2 \quad (6)$$

The relative contributions to $G(\Gamma)$ by the different species are given by the relative intensities of light scattered by the different species. The intensity of scattered light for a species of a particular molar mass M and mass concentration c is given by B. Zimm in *J. Chem. Phys.*, vol. 16, no. 12, 1093-1099 (1948) as $$R = K^* McP(r_g,\theta)[1-2A_2McP(r_g,\theta)] \quad (7)$$

where R is the excess Rayleigh ratio, meaning the ratio of the light scattered from the solute and the incident light intensity, corrected for size of scattering volume and distance from scattering volume. $P(\theta)$ is the form factor or scattering function which relates the angular variation in scattering intensity to the root mean square radius, $r_g$, of the particle. $A_2$ is the second virial coefficient, a measure of solvent-solute and solute-solute interaction and is the second term in the virial expansion of osmotic pressure. $A_2$ enters into the light scattering equation as a correction factor for concentration effects due to intermolecular interactions influencing the scattering light intensity. M is the molar mass, c is the solute concentration in g/mL, and $K^*$ is defined as follows:

$$K^* = \frac{4\pi n_0^2}{N_A\lambda_o^4}\left(\frac{dn}{dc}\right)^2$$

where $n_0$ is the solvent refractive index, $N_A$ is Avagadro's number, $\lambda_0$ is the vacuum wavelength of incident light, and dn/dc is the specific refractive index increment.

For a distribution of species with a distribution of $r_h$ and associated distribution of $\Gamma$, with corresponding distributions of $M(\Gamma)$, $c(\Gamma)$, $r_g(\Gamma)$, and $A_2(\Gamma)$, using equations, 3, 4, 6, and 7, the expected distribution of exponential functions which would be observed in an intensity-intensity autocorrelation DLS measurement may be seen to be $$G(\Gamma) = \frac{R[M(\Gamma), c(\Gamma), r_g(\Gamma), A_2(\Gamma)]}{\int_0^\infty R(M(\Gamma), c(\Gamma), r_g(\Gamma), A_2(\Gamma))d\Gamma}. \quad (8)$$

Equation (8) may be simplified for some cases. If all species involved in the measurement have root mean square radii about a factor of 50 or more smaller than the wavelength of light in the solution being used for measurement (i.e. $r_g<10$ nm for 660 nm light in water), then the scattering function $P(\theta)$ approaches 1.0 regardless of the angle of measurement and may be disregarded. A second simplification may be made for the case where for all species involved in the measurement $2A_2McP(\theta)<<1$, enabling this term including to be neglected. With both these assumptions, the intensity of scattered light from a single species is given by $$R = K^*Mc \quad (9)$$

and Equation (8) simplifies to $$G(\Gamma) = \frac{M(\Gamma)c(\Gamma)}{\int_0^\infty M(\Gamma)c(\Gamma)d\Gamma}. \quad (10)$$

Inventive steps 1 and 2 described above generate a modeled distribution of species, each species having a particular concentration, molar mass, and hydrodynamic radius with associated decay rate. Given that modeled distribution, Equation (8), or if appropriate Equation (10), may be combined with Equation (5) or (6) to generate the modeled field-field or intensity-intensity autocorrelation function, respectively. Using Equation (10), the intensity-intensity autocorrelation function may be seen to be $$g^{(2)}(\tau) = 1 + \beta\left[\frac{\int_0^\infty M(\Gamma)c(\Gamma)\exp(-\Gamma\tau)d\Gamma}{\int_0^\infty M(\Gamma)c(\Gamma)d\Gamma}\right]^2.$$

Step 4: Fitting Modeled DLS Results to DLS Measurements.

Procedure A: Directly Fitting all Autocorrelation Functions

Performing inventive steps 1, 2, and 3 permit the calculation of the expected autocorrelation functions for all samples measured. All autocorrelation functions may thus be fit, either individually or in concert, with association constants, conformation parameters, and hydrodynamic radii as parameters in the fit. In this way the parameters which most accurately represent the data may be determined. Any of the parameters in the fit may be fixed to known values or may be varied as a part of the fitting procedure.

Procedure B: Fitting $G(\Gamma)$

Alternatively, estimates for the distribution $G(\Gamma)$ at each concentration may found from the autocorrelation data, and compared to the modeled $G(\Gamma)$ to determine the best fit parameters. It is not possible to uniquely determine $G(\Gamma)$ from data of $g^{(1)}(\tau)$ or $g^{(2)}(\tau)$, and direct comparison between modeled and measured $G(\Gamma)$ is not possible. However, it is possible to estimate $G(\Gamma)$ from the autocorrelation function using the method of regularization, as discussed by S. W. Provencher in *Makromol. Chem.*, vol. 180, 201-209 (1979), and developed further by many others.

Procedure C: Fitting Derived Quantities

The methods of fitting procedures A and B can be mathematically involved and computationally intensive. Instead, each autocorrelation function may be analyzed separately, generating just one or two derived values which contain most of the information characterizing the distribution $G(\Gamma)$.

Those derived quantities may then be compared to the values expected by the modeling, and the modeled parameters may thus be determined. There are many functional forms used to fit individual autocorrelation functions. One class of functions generally used to fit autocorrelation function data is generated by assuming some functional form for $G(\Gamma)$, such as a Gaussian distribution, and calculating the corresponding expected $g^{(1)}(\tau)$ or $g^{(2)}(\tau)$. For the example of a Gaussian distribution of $G(\Gamma)$, the center and width of the Gaussian distribution are two of the free parameters used when fitting the autocorrelation function data. A second class of functions used to fit autocorrelation function data use an expansion of the distribution $G(\Gamma)$ into moments of the distribution, and calculating the corresponding expected $g^{(1)}(\tau)$ or $g^{(2)}(\tau)$. The most commonly used implementation of this class of functions is the method of cumulants expansion, as described by D. E. Koppel in *J. Chem. Phys.* 57, 4814-4820 (1972). The method of cumulants may be used to fit the autocorrelation data to determine the first and second cumulants, which are identical to the first and second moments of the distribution $G(\Gamma)$. The first and second moments of this distribution are defined as $$\mu_1 = \bar{\Gamma} = \int_0^\infty \Gamma G(\Gamma) d\Gamma \text{ and } \mu_2 = \int_0^\infty (\Gamma - \bar{\Gamma})^2 G(\Gamma) d\Gamma$$

respectively. The first moment is the mean decay rate, and is often designated by the symbol $\bar{\Gamma}$. The second moment is proportional to the width of the distribution $G(\Gamma)$, and is often used in the definition of the polydispersity of a measured sample as $$Pd = \frac{\mu_2}{\mu_1^2}.$$

Both the first and second moments of the modeled distribution $G(\Gamma)$ may be calculated for the models described above and fit to the values for the first and second moment derived from data for all concentrations, and so the modeled parameters may be extracted. Below we provide an example of this procedure for the case of comparing the mean decay rate between the data and models of association.

The mean decay rate $\bar{\Gamma}$ may be used to calculate an equivalent radius spherical species, termed the average hydrodynamic radius, $r_{avg}$. Given species A and B which satisfy the conditions making Equation (9) valid, having molar masses $M_A$ and $M_B$, concentrations $c_A$ and $c_B$, and hydrodynamic radii $r_{hA}$ and $r_{hB}$, with associated translational diffusion coefficients $D_A$ and $D_B$ and corresponding decay rates $\Gamma_A$ and $\Gamma_B$, the function $G(\Gamma)$ is given by $$G(\Gamma) = \frac{\delta(\Gamma - \Gamma_A) M_A c_A + \delta(\Gamma - \Gamma_B) M_B c_B}{M_A c_A + M_B c_B}$$

where $\delta(x)$ is the Dirac delta function having a value of 1 for $x=0$ and 0 otherwise. The mean decay rate becomes $$\bar{\Gamma} = \int_0^\infty \Gamma G(\Gamma) d\Gamma = \frac{\Gamma_A M_A c_A + \Gamma_B M_B c_B}{M_A c_A + M_B c_B}$$

Expressing the decay rates in terms of the equivalent hydrodynamic radii and cancelling common terms, we find $$\frac{1}{r_{avg}} = \frac{(1/r_A) M_A c_A + (1 + r_B) M_B c_B}{M_A c_A + M_B c_B}$$

Where $r_{avg}$ is the hydrodynamic radius corresponding to the mean decay rate $\bar{\Gamma}$. This may be rewritten as $$r_{avg} = \frac{M_A c_A + M_B c_B}{(M_A c_A / r_A) + (M_B c_B / r_B)}$$

We may extended this analysis for an arbitrary number of species to $$r_{avg} = \frac{\sum_i M_i c_i}{\sum_i M_i c_i / r_i} \quad (11)$$

Equation (11) is specific for the case of validity of Equation (9), but may be expressed more generally by substituting Equation (7) for Equation (9) during the derivation.

Example of Steps 1-4:

As an example of the inventive method, we consider two species A and B associating to form species AB with equilibrium association constant $K_{AB}$: $A+B \rightleftharpoons AB$. In this example we will use fitting procedure C, using the average hydrodynamic radius found by fitting the autocorrelation function measured for each sample to a cumulants model. We will assume that Equation (11) is valid. The mass concentrations used in Equation (11) are given by multiplying the molar concentrations by the molar mass of each species, giving $$r_{avg} = \frac{M_A^2 [A] + M_B^2 [B] + (M_A + M_B)^2 [AB]}{(M_A^2 [A]/r_A) + (M_B^2 [B]/r_B) + ((M_A + M_B)^2 [AB]/r_{AB})}$$

The modeled molar concentrations for A and B, and AB are given by the following equations in terms of total molar concentrations $[A_{tot}]$ and $[B_{tot}]$ as $$[B] = \frac{1}{2} \Big\{ ([B_{tot}] - [A_{tot}]) -$$

$$\frac{1}{K_{AB}} \Big( 1 - \{1 + 2K_{AB}([B_{tot}] + [A_{tot}]) + K_{AB}^2 [B_{tot}] - [A_{tot}])^2 \}^{\frac{1}{2}} \Big) \Big\}$$

$$[A] = \frac{[A_{tot}]}{(1 + K_{AB}[B])}$$

and $[AB] = K_{AB}[A][B]$. Given hydrodynamic radii $r_A$ and $r_B$, for this example we will assume $r_{AB} = \{r_A^a + r_B^a\}^{1/a}$. If molar masses $M_A$ and $M_B$ and hydrodynamic radii $r_A$ and $r_B$ are assumed known, and $[A_{tot}]$ and $[B_{tot}]$ are known from sample preparation, then association constant $K_{AB}$ and the association conformation parameter a are the only free parameters in a fit between the data and the model.

The high throughput screening may follow the complete characterization of the interaction. Alternatively, once the molar ratio/concentration showing the maximum hydrodynamic radius is determined, full characterization may be bypassed if the sole point of interest is discovery of a protein protein interaction inhibitor/promoter/effector. Or, a ratio/concentration of the particles may be chosen based on other criteria.

The library may be added before or after the addition of the protein solution to the plate. The optimal mixture of protein 'A' and protein 'B,' may then be placed in the wells of a microtiter plate. The hydrodynamic radius of each well would then be measured. The plate may be measured in the DLS plate reader immediately, or after a set period to allow the reaction with the library compounds to occur. Alternately, the plate could be scanned continuously over a set time period. Depending on the time constant of the potential inhibition, the change in the hydrodynamic radius may be possible to monitor through time, and the kinetics of the interaction quantified. Sample holding systems are not limited to multiwell plates. Other systems may be used as well.

Additional Application:

Measuring the equilibrium constant over a series of temperatures can yield thermodynamic information about the association: At equilibrium, there is no net change in the Gibbs free energy of a system, and the relationship of $\Delta G°$, the free energy change of a reaction when all its reactants and products are in their standard states, can be written as:

$$\Delta G° = -RT \ln K_{eq}$$

where R is the ideal gas constant, and T is absolute temperature. Substituting in the Gibbs free energy at constant temperature and pressure, where H and S reflect enthalpy and entropy, respectively: $\Delta G° = \Delta H° - T\Delta S°$, yields the manner in which the equilibrium constant varies with temperature:

$$\ln K_{eq} = -\frac{\Delta H°}{R}\left(\frac{1}{T}\right) + \frac{\Delta S°}{R}$$

The derivation of this function as described by D. Voet et al., *Biochemistry*, 2nd Ed John Wiley & Sons, Inc., New York, N.Y., (1995) Chapter 3, affects the reasonable assumption that $\Delta H°$ and $\Delta S°$ are independent of temperature. A plot of ln $K_{eq}$ vs. 1/T yields a straight line of slope $-\Delta H°/R$ and an intercept of $\Delta S°/R$. The plot, known as a van't Hoff plot, enables the values of $\Delta H°$ and $\Delta S°$ to be determined from measurements of $K_{eq}$ at two or more temperatures.

Further Examples

Having fully described the invention above, the following examples are given solely for illustrative purposes and are not intended to limit the scope of the invention in any manner.

Figure 3:
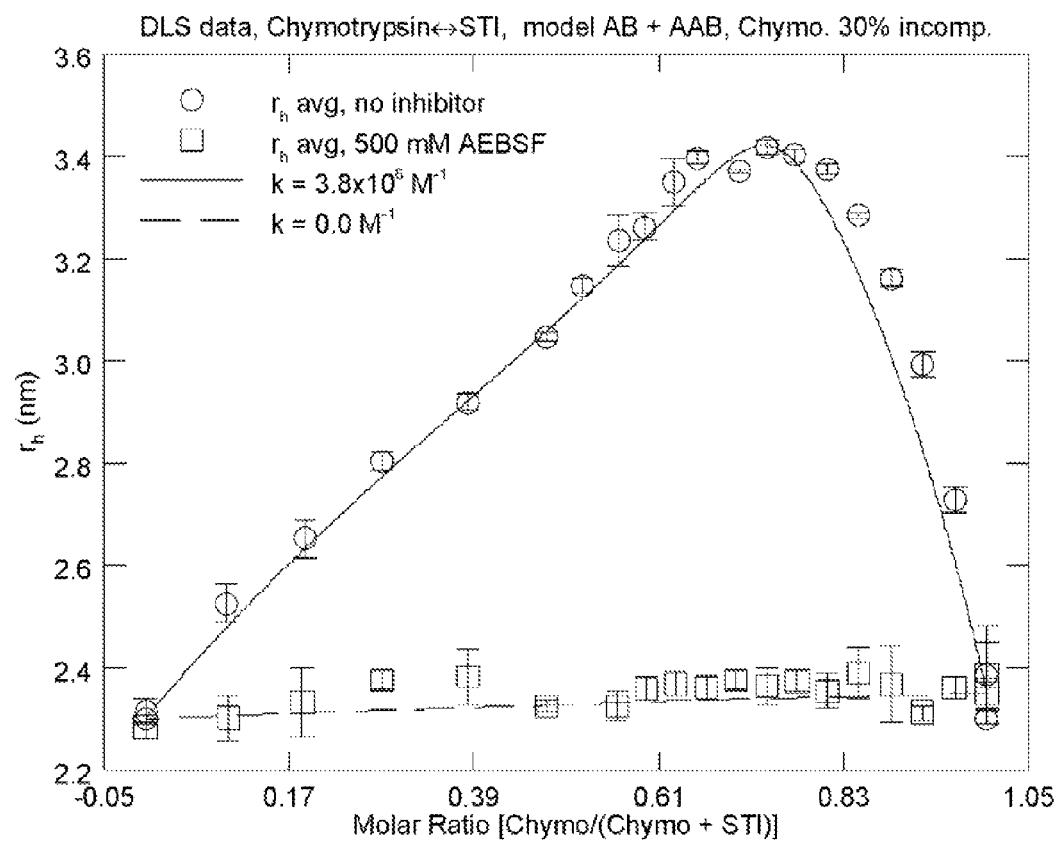
FIG. 3 shows results obtained from protein heteroassociation experiments indicating binding and stoichiometry for chymotrypsin and soybean trypsin inhibitor. No binding is found in the presence of the inhibitor AEBSF.

In FIG. 3 the soybean trypsin inhibitor (molar mass of 22 kDa) and chymotrypsin (molar mass of 25 kDa) heteroassociation experiment results are shown. The $r_h$ is plotted as a function of the molar ratio of the two proteins. Circle symbols show the data, the solid line shows the fit. This data was fitted with an incompetent fraction of chymotrypsin, meaning that it was assumed that a portion of the chymotrypsin in solution is unable to associate with the soybean trypsin inhibitor. The soybean trypsin binding site on chymotrypsin is known to possess some heterogeneity, as shown by Erlanger et al. in their 1970 paper, "Operation Normality of α-Chymotrypsin solutions by a sensitive potentiometric technique using a fluoride electrode", *Analytical Biochemistry*, 33, 318-322. Incorporating an incompetent fraction into the fitting allows for the exclusion of the non-participating enzyme fraction. For this heteroassociation, the association constant was found to be $3.8 \times 10^6 M^{-1}$, with a corresponding a value of 2.26. The binding stoichiometry was found to be 2:1 chymotrypsin:soybean trypsin inhibitor, in accordance with the known association ratio.

The additional data set in FIG. 3, represented by open squares, is the same experiment repeated in the presence of 500 mM 4-(2-Aminoethyl) benzenesulfonyl fluoride hydrochloride (AEBSF). AEBSF, is a small molecule known to be a serine protease inhibitor which binds to the chymotrypsin active site, thus inhibiting the binding of the soybean trypsin inhibitor. Since AEBSF is a small molecule ($r_h \ll 1$ nm), the decay rate of the autocorrelation function associated with AEBSF is faster than may be observed with conventional DLS technology, and the presence of that molecule is not observed in the DLS signal. When AEBSF associates with chymotrypsin, the $r_h$ of the associated species is not measurable different from that of unassociated chymotrypsin. The increase in $r_h$ seen in the absence of AEBSF is not observed in this experiment. This shows that the increase in $r_h$ is due to specific site binding of the two proteins, an interaction which is completely inhibited by AEBSF. This negative control also demonstrates the potential of the technique for large scale screening of small molecule modulators of particle—particle associations. Additionally, the association constant of AEBSF with chymotrypsin may be measured using this invention by repeating the chymotrypsin/soybean trypsin inhibitor/AEBSF experiment and lowering the concentration of AEBSF until some increase in $r_h$ is seen, and modeling the associating species.

Figure 4:
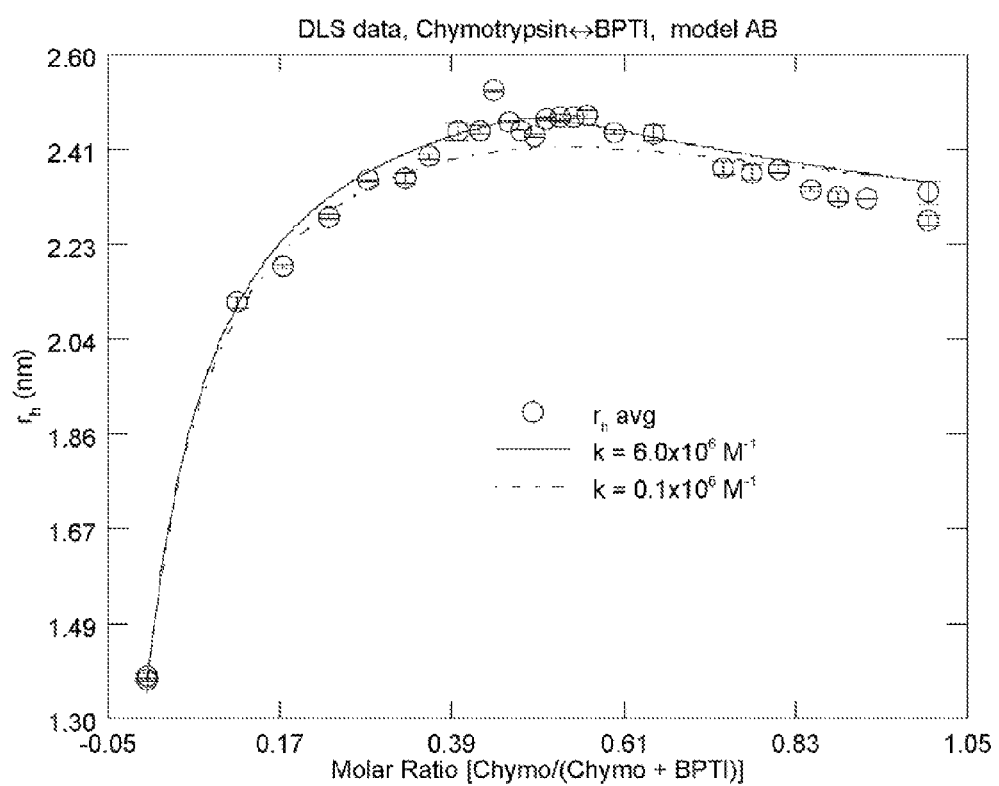
FIG. 4 shows results obtained from a protein heteroassociation experiment indicating binding and stoichiometry for chymotrypsin and bovine pancreatic trypsin inhibitor.

In FIG. 4 the bovine trypsin inhibitor (6.5 kDa) and chymotrypsin heteroassociation experiment results are shown. The $r_h$ is plotted as a function of the molar ratio of the two proteins. Circle symbols show the data, while the solid line shows the fit. For this heteroassociation, the data were found to be consistent with an association constant of $6 \times 10^6 M^{-1}$ with an a value of 3, and the binding stoichiometry was found to be 1:1 chymotrypsin:bovine trypsin inhibitor, in accordance with the known association ratio. This association constant value closely matches the $6.3 \times 10^6 M^{-1}$ value reported by Kameyama et al., *Biophysical Journal*, Vol. 90, 2164-2169, (2006), who analyzed the two proteins in the same buffer conditions, using static light scattering. For comparison, a fit using association constants of $0.1 \times 10^6 M^{-1}$ is shown by broken lines. For these data, higher association constants (up to infinity) fit the data equally well as the solid line shows, and so in this case it is possible only to provide a minimum value for the association constant.

Figure 5:
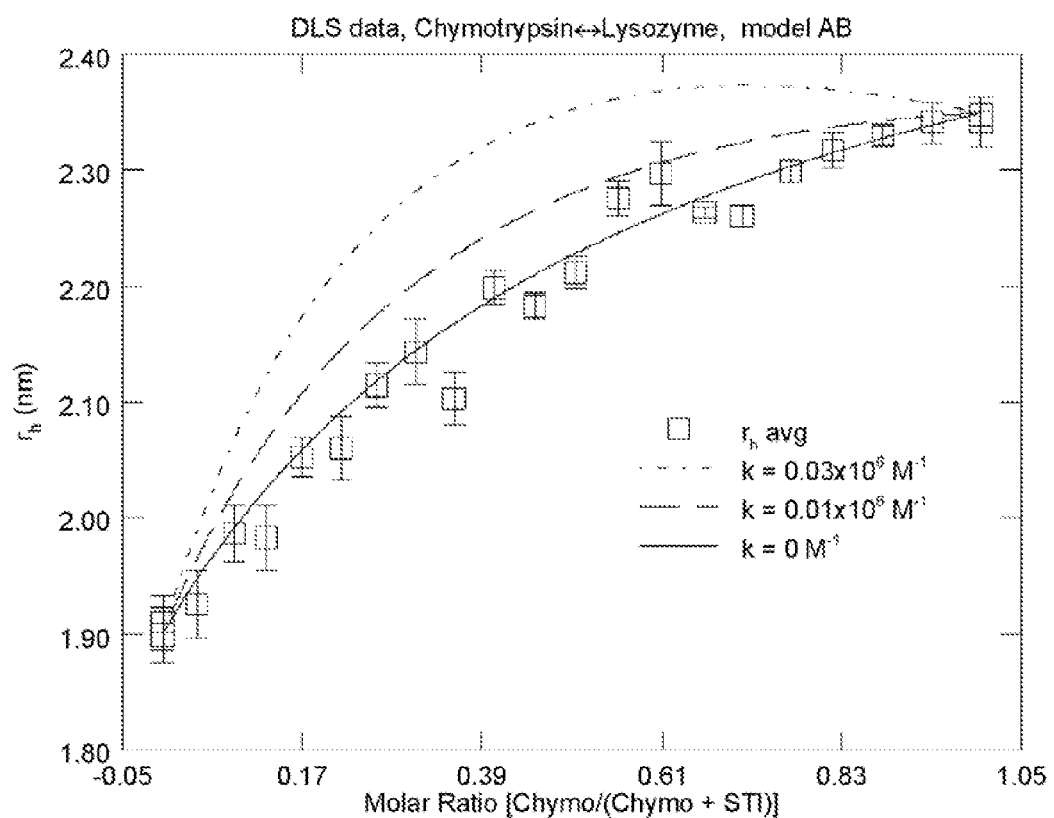
FIG. 5 shows the results of a heteroassociation negative control experiment. The data are consistent with no binding between chymotrypsin and lysozyme.

In FIG. 5 the negative control of chymotrypsin and lysozyme (14.4 kDa) is shown. The $r_h$ is plotted as a function of the molar ratio of the two proteins. Open square symbols show the data, while the solid line shows the fit. Although the two proteins are oppositely charged under the experimental conditions of pH 6.7, the association constant is found to be 0, reflecting an absence of any specific interaction. This control shows that only proteins with specific binding will be detected in this technique; non-associating proteins will not yield an association constant.

Figure 6:
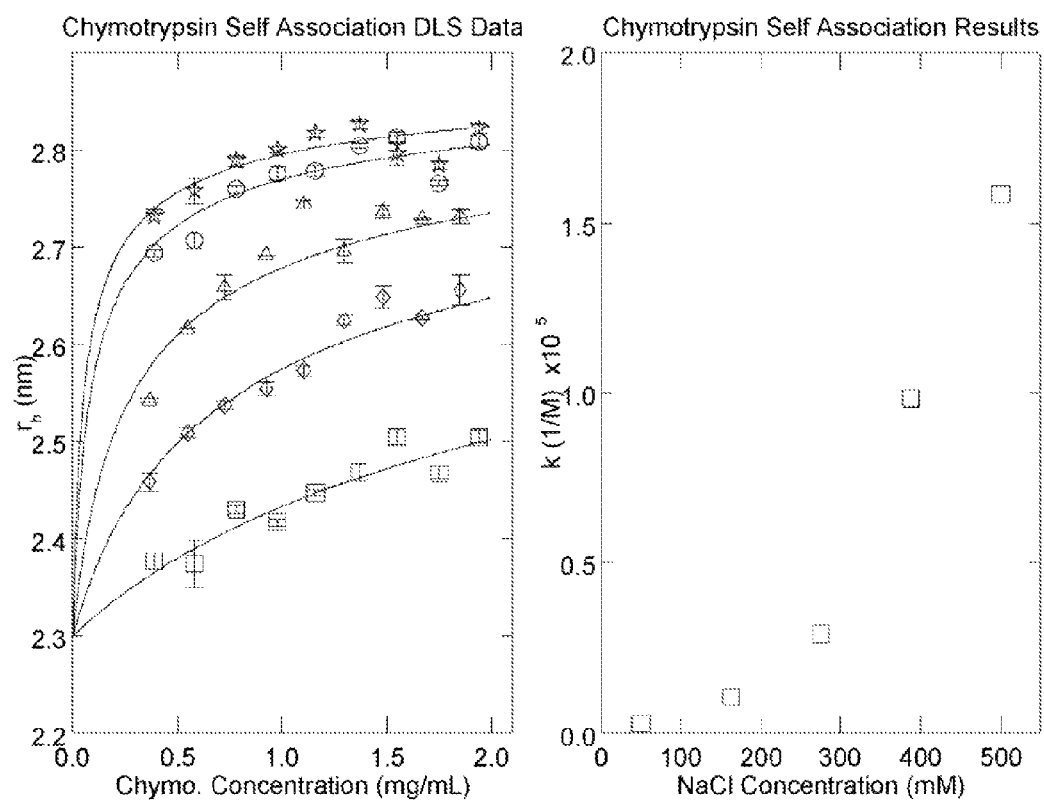
FIG. 6 shows the results of a series of chymotrypsin self association experiments at differing solution salinities.

In FIG. 6, results of self-association experiments are shown. Here, the association constant for the dimerization of α-chymotrypsin is determined as a function of buffer salinity. On the left graph, the $r_h$ is plotted as a function of the protein concentration. Open symbols show the data, while solid lines indicate the fits. Squares, diamonds, triangles, circles, and stars represent data with solution concentrations of 50, 162.5, 275, 387, and 500 mM NaCl respectively. Note as the salinity increases, the $r_{avg}$ increases, corresponding to an increase in association constant. The fitted association constants extracted from each data set are graphed on the right, as a function of sodium chloride concentration. Values closely match those determined with static light scattering, as reported by M. Larkin and P. Wyatt in chapter 8 of *Formulation and Process Development Strategies for Manufacturing of a Biopharmaceutical*, John Wiley & Sons, Inc., New York, N.Y., in press 2008.

Many embodiments of this invention that will be obvious to those skilled in the art of dynamic light scattering measurements, particle interactions, or high throughput screening are but simple variations of the basic invention herein disclosed. Accordingly,

We claim:

1. A method to characterize and measure the equilibrium self-association constants of a molecular species and its underlying stoichiometries within a given solvent comprising the steps of
   1. collecting dynamic light scattering data from a plurality of samples spanning range of varying concentrations of said molecular species in said solvent comprising the steps of
      A. preparing a concentration series of a plurality samples of varying known concentrations of said molecular species in said given solvent;
      B. illuminating each member of said concentration series with a light beam from a laser source;
      C. measuring the intensity fluctuations of light scattered by each said member of said molecular concentration series; and
      D. deriving an experimentally derived scattered light correlation function from each said measured member;
   2. modeling theoretical light scattering data comprising the steps of
      A. postulating a plurality of possible stoichiometries of the self-associating species that may be present within each of said members of said concentration series;
      B. parameterizing the concentrations of each self-associating and non-associating species within each member of said concentration series; and
      C. parameterizing the hydrodynamic radii of each self-associating species;
   3. comparing said experimentally derived scattered light correlation functions from said plurality of samples to said modeled theoretical light scattering data for each of said possible stoichiometries that may be present within each member of said concentration series comprising the steps of
      A. calculating modeled theoretical scattered light correlation functions from said modeled theoretical light scattering data for each said postulated stoichiometry and said parametrized concentrations and said parametrized hydrodynamic radii; and
      B. obtaining a best fit of said experimentally derived scattered light correlation functions from each said concentration series member to each of said modeled theoretical light scattering correlation function, and
   4. deriving from said best fit the equilibrium association constants of said self-associations and their corresponding stoichiometries.

2. The method of claim 1 where said concentration series is produced by the successive dilution of an initial highest concentration of said molecular species, said dilution achieved using a stock solution of said solvent.

3. The method of claim 2 further comprising the step of adding a corresponding concentration of a second molecular species to some members of said concentration series.

4. The method of claim 1 further comprising the step of modeling each parameterized hydrodynamic radius of each complex by using the hydrodynamic radii of said complex's constituent molecules.

5. The method of claim 1 wherein said concentration series consists of 10 to 20 members.

6. The method of claim 1 wherein said postulated hydrodynamic radii are fixed values determined a priori.

7. The method of claim 1 wherein said postulated concentrations are fixed values determined a priori.

* * * * *